United States Patent [19]

Matsuo et al.

[11] Patent Number: 4,504,401
[45] Date of Patent: Mar. 12, 1985

[54] STAINPROOFING AGENT AND PROCESS FOR ITS PREPARATION

[75] Inventors: Masashi Matsuo; Katsuji Itoh, both of Yokohama; Takao Hayashi, Zushi; Yoshio Oda, Yokohama, all of Japan

[73] Assignee: Asahi Glass Company Ltd., Tokyo, Japan

[21] Appl. No.: 521,407

[22] Filed: Aug. 8, 1983

[30] Foreign Application Priority Data

Aug. 20, 1982 [JP] Japan ............... 57-143463

[51] Int. Cl.³ .................. D06M 13/28; D06M 13/40
[52] U.S. Cl. ..................... 252/8.75; 252/8.8
[58] Field of Search ................ 252/8.8, 8.75

[56] References Cited

U.S. PATENT DOCUMENTS 3,398,182 8/1968 Guenthner et al. ............ 252/8.75
3,896,035 7/1975 Schultz et al. ............... 252/8.75
3,996,281 12/1976 Huber-Emden et al. .......... 252/8.8
4,043,923 8/1977 Loudas ....................... 252/8.8

Primary Examiner—Maria Parrish Tungol
Attorney, Agent, or Firm—Oblon, Fisher, Spivak, McClelland & Maier

[57] ABSTRACT

A stainproofing agent containing as an active ingredient a polyfluoroalkyl group-containing compound represented by the following general formula and having a molecular weight of from 800 to 3000:

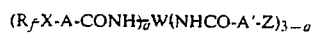

$$(R_f\text{-}X\text{-}A\text{-}CONH)_a W(NHCO\text{-}A'\text{-}Z)_{3-a}$$

where $R_f$ is a polyfluoroalkyl group having from 1 to 20 carbon atoms, X is $-R-$, $-CON(R^1)-Q-$ or $-SO_2N(R^1)-Q-$ (where R is a divalent alkylene group, $R^1$ is a hydrogen atom or a lower alkyl group and Q is a divalent organic group), each of A and A' is $-O-$, $-S-$ or $-N(Z')-$ (where Z' is a hydrogen atom or a monovalent organic group), Z is a monovalent organic group, W is a trivalent organic group, a is an integer of 1, 2 or 3. A process for the stainproofing agent is also disclosed.

7 Claims, No Drawings

STAINPROOFING AGENT AND PROCESS FOR ITS PREPARATION

BACKGROUND OF THE INVENTION

1. Field of the Invention

The present invention relates to a novel stainproofing agent containing a certain specific polyfluoroalkyl group-containing compound as an active ingredient and a process for its preparation.

2. Description of the Prior Art

Heretofore, in the treatment of fiber products such as woven fabrics or carpets with a treating agent having a polyfluoroalkyl group (hereinafter referred to as a "PFA group"), it has been common to employ a method wherein the treating agent is coated on the surface of the fiber product by means of an aqueous emulsion or organic solvent solution of an acrylate-type high molecular weight polymer. However, such a high molecular weight treating agent constitutes a non-continuous phase held on the fiber surface mainly by physical adhesive power, and consequently tends to be abraded off when the fibers are subjected to mechanical actions during the processing to a final product or during the use as the fiber product. Further, the high molecular weight treating agent having a PFA group has a deficiency in its effectiveness to impart a stainproofing property such as an anti-dry soil property which is important particularly for the treatment of carpets.

There have been proposed various means to overcome the above-mentioned deficiency of the high molecular weight treating agent. For instance, it has been proposed to use as a treating agent a low molecular weight fluorinated compound composed of a derivative of e.g. phthalic acid, terephthalic acid, trimellitic acid or pyromellitic acid. (See U.S. Pat. Nos. 3,646,153, 3,870,748 and 4,209,610.) Further, as a material useful as a stainproofing agent for e.g. carpets, various fluorine-containing urethane compounds having PFA groups have been proposed, for instance, in U.S. Pat. No. 3,398,182 and Japanese Unexamined Patent Publications No. 112,855/1978 and No. 74,000/1979.

The present inventors have now found that a relatively low molecular weight compound obtained by reacting e.g. a PFA group-containing alcohol to a trifunctional isocyanate compound, effectively overcomes the deficiencies of the above-mentioned high molecular weight treating agent and is superior in its abrasion durability to a low molecular weight fluorinated compound such as the conventional fluorine-containing urethane compound. Such a specific compound has a molecular weight of from 800 to 3000 and contains at least three urethane bonds or urea bonds as well as at least one PFA group. Such a PFA group-containing specific compound may be used prior to the dyeing step and is also advantageously be used as a treating agent at the time of spinning base yarns for fiber products such as carpets. The specific treating agent of the present invention is capable of providing a stainproofing property when used at the time of spinning and will not fall off from the fiber products even during the dyeing step and does not adversely affect the dyeing.

SUMMARY OF THE INVENTION

The present invention provides a stainproofing agent containing as an active ingredient a polyfluoroalkyl group-containing compound represented by the following general formula and having a molecular weight of from 800 to 300:

$$(R_f\text{—}X\text{—}A\text{—}CONH)_a\text{—}W\text{—}(NHCO\text{—}A'\text{—}Z)_{3-a} \quad (I)$$

where $R_f$ is a polyfluoroalkyl group having from 1 to 20 carbon atoms, X is —R—, —CON(R$^1$)—Q— or —SO$_2$N(R$^1$)—Q— (where R is a divalent alkylene group, R$^1$ is a hydrogen atom or a lower alkyl group and Q is a divalent organic group), each of A and A' is —O—, —S— or —N(Z')— (where Z' is a hydrogen atom or a monovalent organic group), Z is a monovalent organic group, W is a trivalent organic group, a is an integer of 1, 2 or 3.

It has also been found that a stainproofing agent having particularly good water repellency can be obtained by reacting a trifunctional isocyanate compound with a combination of a PFA group-containing alcohol and n—C$_{18}$H$_{37}$OH, n—C$_{18}$H$_{37}$NH$_2$ or n—C$_{18}$H$_{37}$SH. Namely, a relatively low molecular weight compound thus obtained which contains at least one PFA group and at least one straight chain stearyl group (hereinafter sometimes referred to as "C$_{18}$H$_{37}$") and which further contains at least three urethane bonds, urea bonds or thiourethane bonds, is capable of imparting especially good water and oil repellency and stainproofing property and it also provides a superior abrasion durability.

DESCRIPTION OF THE INVENTION

The present invention provides a preferred stainproofing agent which contains as an active ingredient a polyfluoroalkyl group-containing compound represented by the general formula:

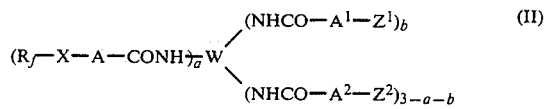

where $R_f$, X, A and W are as defined above, each of A$^1$ and A$^2$ is —O—, —S— or —N(Z')— (where Z' is as defined above), Z$^1$ is a straight chain stearyl group, Z$^2$ is a monovalent organic group, a is an integer of 1 or 2 and b is an integer of 1 or 2.

According to the study of the present inventors, when a diisocyanate (OCN—Y—NCO) is reacted with water, a dimer of OCN—Y—NHCONH—Y—NCO is formed. When reacted with a monomer of OCN—Y—NCO, such a dimer forms a trimer of

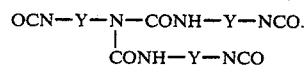

Further, when two such dimers are reacted with each other, a tetramer of

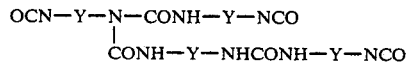

is formed. Likewise, when the dimer and the trimer are reacted, a pentamer is formed. In a similar fashion, various polymers will be formed. By such an addition reaction of a >N—H group with a —NCO group, a mixture of polyfunctional isocyanate compounds having at least three —NCO groups is obtainable. For instance, the above-mentioned trimer or tetramer has three —NCO groups, and the tetramer obtained by the reaction of the monomer with the trimer or the pentamer obtained by the reaction of the dimer with the trimer, has four —NCO groups.

The present inventors have found that when e.g. a PFA group-containing alcohol is reacted to the mixture of polyfunctional isocyanate compounds having at least three —NCO groups, it is possible to obtain a mixture of relatively low molecular weight PFA-containing compounds, and the mixture thereby obtained effectively overcomes the above-mentioned deficiency of the high molecular weight treating agent and is superior in the abrasion durability to a low molecular weight fluorinated compound such as the conventional fluorine-containing urethane compounds. The specific compounds contained in the mixture have a molecular weight of at most 8000 and contain at least three —NHCO-groups and at least one PFA group. At least one of —NCO groups in the polyfunctional isocyanate compound is converted to a group containing a PFA group, and the rest of the —NCO groups are converted to PFA group-containing groups or other organic groups.

The mixture of the PFA group-containing compounds thus obtained is useful as a treating agent at the time of spinning base yarns for fiber materials such as carpets. Namely, the mixture is capable of imparting a stainproofing property when used at the time of spinning, and will not fall off from the fiber products during the dyeing step and does not adversely affect the dyeing.

The present invention also provides a process for preparing a stain proofing agent, which comprises reacting a mixture of polyfunctional isocyanate compounds having at least three —NCO groups and a —NHCON bond derived from an addition reaction of a >N—H group-containing compound with a —NCO group-containing compound, with a compound represented by the general formula $R_f$—X—A—H where $R_f$ is a polyfluoroalkyl group having from 1 to 20 carbon atoms, X is —R—, —CON($R^1$)—Q— or —SO$_2$N($R^1$)—Q— (where R is a divalent alkylene group, $R^1$ is a hydrogen atom or a lower alkyl group and Q is a divalent organic group) and A is —O—, —S— or —N(Z')— (where Z' is a hydrogen atom or a monovalent organic group), and, if required, further reacting the mixture with a compound represented by the general formula Z—A'—H where H is a monovalent organic group and A' is —O—, —S— or —N(Z')— (where Z' is a hydrogen atom or a monovalent organic group), to form a mixture of polyfluoroalkyl group-containing compounds having at least one —NHCO—A—X—$R_f$ group where A, X and $R_f$ are as defined above, a molecular weight of at most 8000 and, if required, at least one —NHCO—A'—Z group where A' and Z are as defined above, provided that the total of the —NHCO—A—X—$R_f$ groups and the —NHCO—A'—Z groups is at least three.

Now, the present invention will be described in detail with reference to the preferred embodiments.

DESCRIPTION OF THE PREFERRED EMBODIMENT

In the above general formulas, $R_f$ is a straight chain or branched polyfluoroalkyl group having from 1 to 20 carbon atoms, preferably from 4 to 16 carbon atoms. It is usual to choose a compound having a perfluoroalkyl group at its terminal. However, the terminal group may not necessarily be a perfluoroalkyl group and may be a hydrogen atom, a chlorine atom or an oxyperfluoroalkylene-containing group. $R_f$ is preferably a perfluoroalkyl group represented by the general formula —$C_nF_{2n+1}$ where n is an integer of 4 to 16, more preferably from 6 to 12.

X is —R—, —CON($R^1$)—Q— or —SO$_2$N($R^1$)—Q— (where R is a divalent alkylene group, $R^1$ is a hydrogen atom or a lower alkyl group and Q is a divalent organic group), X is preferably a divalent alkylene group having from 1 to 10 carbon atoms, preferably from 2 to 4 carbon atoms, represented by the general formula —$C_mH_{2m}$— (where m is an integer of 1 to 10, preferably 2 to 4). Q is a divalent organic group, and is preferably a divalent alkylene group of the formula —R—.

Each of A and A' is —O—, —S— or —N(Z')— (where Z' is a hydrogen atom or a monovalent organic group). From the viewpoint of availability, A is preferably —O— and A' is preferably —O— or —N(Z')—. Likewise, referring to the general formula II, each of A, $A^1$ and $A^2$ is —O—, —S— or —N(Z')—. From the viewpoint of availability, however, it is preferred that A is —O—, $A^1$ is —O— and $A^2$ is —O— or —N(Z')—.

Z is a monovalent organic group and may be the same as the above-mentioned Z', or Z may together with Z' form a ring. Likewise, referring to the general formula II, $Z^2$ is a monovalent organic group and may be the same as Z', or it may together with Z' form a ring. For instance, each of —A'—Z and —$A^2$—$Z^2$ is preferably —OR' (where R' is an alkyl group),

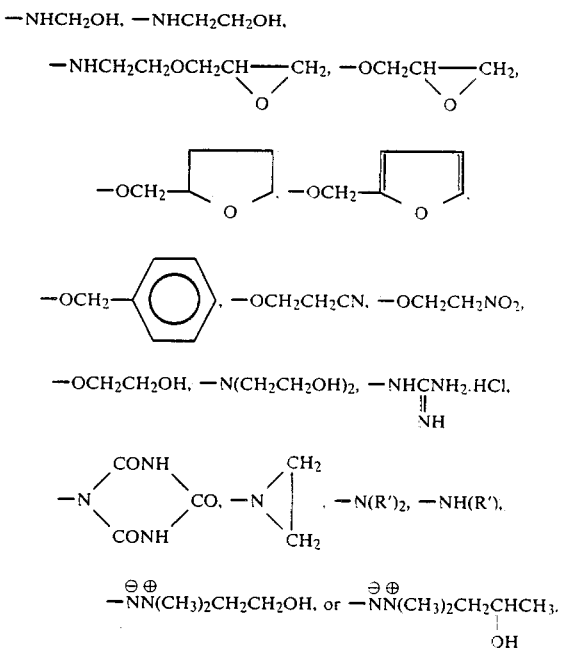

Referring to the preferred PFA group-containing compounds represented by the general formula II, $Z^1$ is a straight chain stearyl group. The effect of the present invention, particularly the effect for the improvement of the water repellency, is especially remarkable when $Z^1$ is a straight chain stearyl group as compared with the case where it is a branched alkyl group or a lower alkyl group.

In the PFA group-containing compounds of the general formula I, W is a trivalent organic group, and a is an integer of 1 to 3. Such PFA group-containing compounds should have a molecular weight of from 800 to 3000, preferably from 1000 to 2000. If the molecular weight is too high, the durability of the stainproofing effect tends to be poor, and there will be certain difficulties in their use prior to the dyeing step or during the spinning of the base yarns. The derivatives obtained from trifunctional isocyanate compounds according to the present invention are superior in the above-mentioned durability to the derivatives obtained from difunctional isocyanate compounds such as relatively low molecular weight fluorine-containing urethane compounds.

In the present invention, the PFA group-containing compounds include those wherein a is 3. However, with a view to a further improvement of the durability by adequate adhesion of the compound to the surface of synthetic fibers, a is preferably 1 or 2 and the compound contains at least one —NHCO—A'—Z group. Usually, the PFA group-containing compounds of the general formula I are prepared by reacting a fluorine-containing compound of $R_f$—X—A—H and a compound of Z—A—H to a trifunctional isocyanate compound of

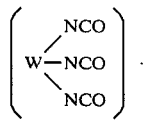

In the preferred PFA group-containing compounds of the general formula II, a is an integer of 1 or 2 and b is an integer of 1 or 2. The preferred PFA group-containing compounds include those wherein a+b is 3. However, with a view to a further improvement of the durability by adequate adhesion of the compound on the surface of the synthetic fibers, a+b is preferably 2, and the compound preferably contains at least one —NH-CO—A²—Z². The preferred PFA group-containing compounds of the general formula II are usually prepared by reacting a fluorine-containing compound of $R_f$—X—A—H, a stearyl group-containing compound of $C_{18}H_{37}$—A¹—H and a compound of Z²—A²—H to a trifunctional isocyanate compound of

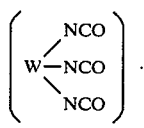

Specific examples of the PFA group-containing compound of the general formula I will be given below.

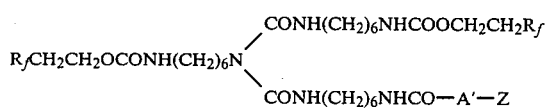

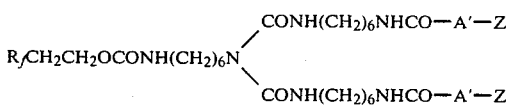

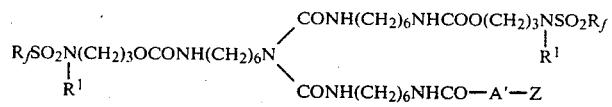

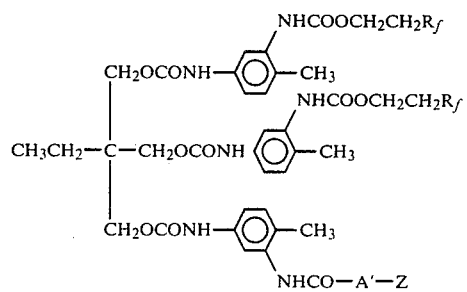

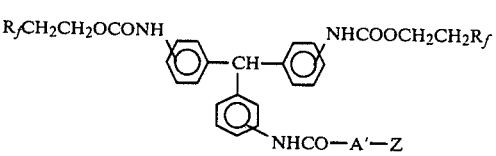

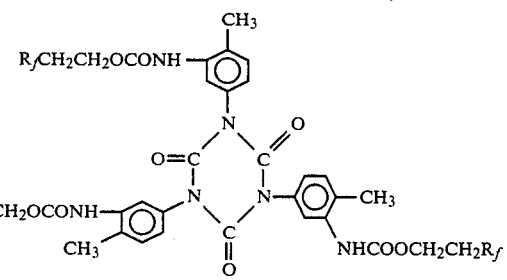

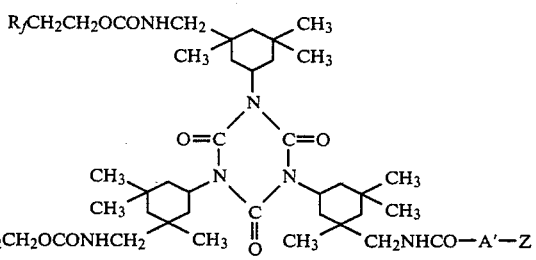

Specific examples of the preferred PFA group-containing compound of the general formula II will be given below.

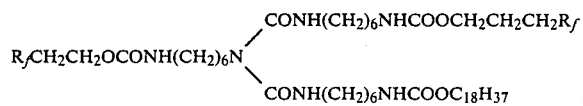

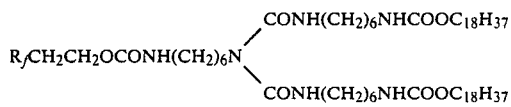

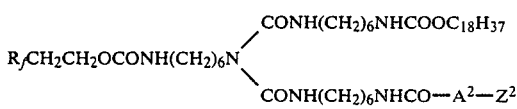

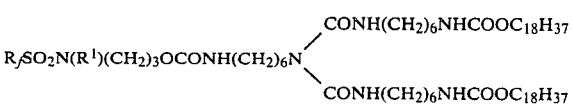

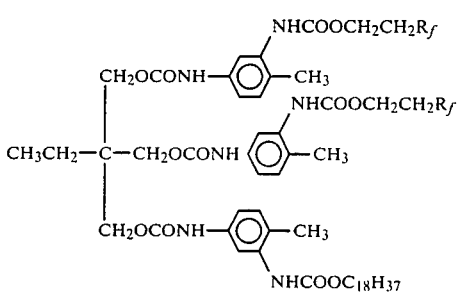

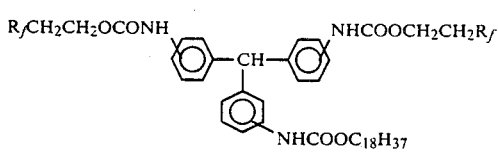

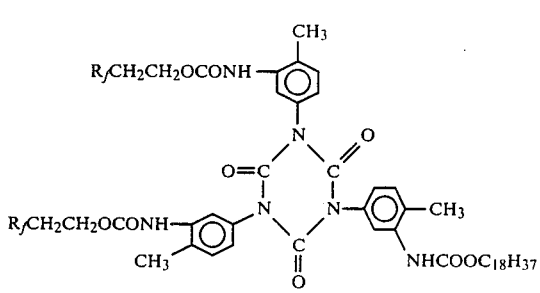

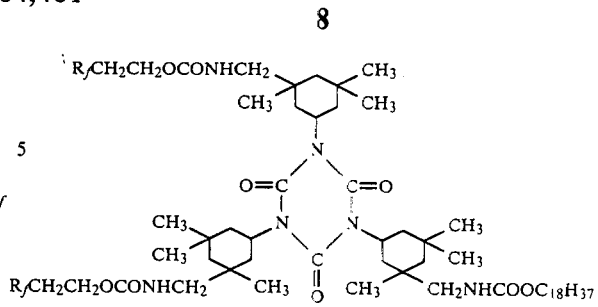

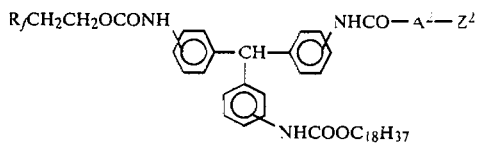

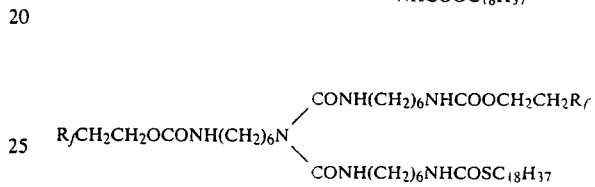

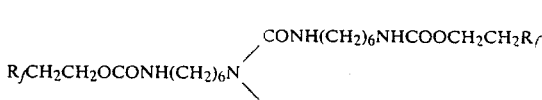

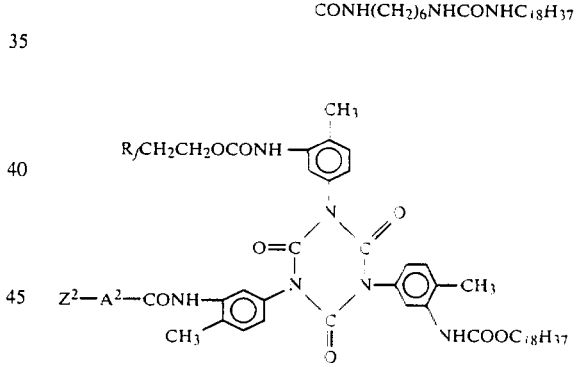

Now, the process for preparing a stainproofing agent composed of a mixture of PFA group-containing compounds, according to the present invention will be described.

In the process of the present invention, it is important to use a mixture (hereinafter referred to simply as an "isocyanate mixture") of polyfunctional isocyanate compounds having at least three —NCO groups. Such a isocyanate mixture is a mixture of compounds containing a —NHCON< bond formed by an addition reaction of a >NH group-containing compound with a —NCO group-containing compound, and is usually advantageously be prepared by reacting and polymerizing a diisocyanate (OCN—Y—NCO) with an active hydrogen atom-containing compound such as water or an amine. Namely, if, for instance, the isocyanate is reacted with water, a dimer of OCN—Y—NHCONH—Y—NCO will be formed, and such a dimer will be reacted as a >NH group-containing compound with a —NCO group of the diisocyanate or the formed polyisocyanate to form various polyfunctional isocyanate compounds. Y is not particularly critical and various divalent organic groups may be used as Y. For instance, as specific examples of OCN—Y—NCO, there may be mentioned aromatic diisocyanates such as 2,4-tolylenediisocyanate, 4,4'-diphenylmethanediisocyanate, tolidinediisocyanate and dianisidinediisocyanate; alicyclic diisocyanates such as 2-methyl-cyclohexane-1,4-diisocyanate, isophoronediisocyanate and hydrogenated MDI

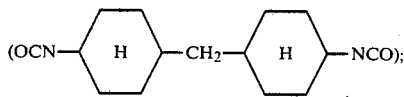

and aliphatic diisocyanates such as hexamethylene diisocyanates and decamethylene diisocyanates.

There is no particular restriction as to the conditions for the preparation of the isocyanate mixture by the above-mentioned polymerization reaction, and various conditions may be employed. For instance, in the case where water is reacted to OCN—Y—NCO, the reaction may be conducted in a molar ratio of $H_2O$/OCN—Y—NCO=3/10 at a temperature of from 100° to 150° C. in the absence of a catalyst when Y is an aromatic group or in the presence of a tertiary amine or a tin catalyst when Y is an aliphatic group.

The isocyanate mixture to be used in the present invention is not restricted to the above-mentioned mixture. For instance, it may be prepared by the synthesis in which various triisocyanate compounds are used. The isocyanate mixture is only required to be a mixture of polyfunctional isocyanate compounds having at least three —NCO groups, and usually contains from 10 to 90% by weight, preferably from 30 to 60% by weight of trifunctional isocyanate compounds (i.e. containing three —NCO groups). The isocyanate mixture preferably contains from 10 to 90% by weight, more preferably from 40 to 70% by weight of at least tetrafunctional isocyanate compounds (i.e. containing at least four —NCO groups). Further, the molecular weights of the polyfunctional isocyanate compounds in the isocyanate mixture are selected so that the molecular weights of the PFA group-containing compounds thereby obtainable become to be at most 8000. The isocyanate mixture may, of course, contain a diisocyanate so long as the latter does not hinder the effect of the present invention. Thus, the polyfunctional isocyanate compounds in the isocyanate mixture may usually contain from 3 to 15 —NCO groups, preferably from 3 to 8 —NCO groups.

In the present invention, a mixture of PFA group-containing compounds having a molecular weight of at most 8000 and containing at least one —NHCO—A—X—$R_f$ group is obtained by reacting a fluorine-containing compound of $R_f$—X—A—H to the above-mentioned isocyanate mixture. As such $R_f$—X—A—H, a $R_f$—R—OH type fluorine-containing alcohol is preferably employed. Further, a $R_f$—R—SH type fluorine-containing thioalcohol where A is —S—, may also be employed. It is also possible that by using as a starting material a mixture of a plurality of fluorine-containing alcohols having different number of carbon atoms in $R_f$ or different R, the desired PFA group-containing compounds are prepared in the form of a mixture.

Thus, in the present invention, a fluorine-containing compound of $R_f$—X—A—H is reacted to the —NCO groups of the polyfunctional isocyanate compounds in the isocyanate mixture. However, it is not necessarily required to convert all of the —NCO groups of the polyfunctional isocyanate compounds to —NHCOAX$R_f$ groups. If required, in addition to the fluorine-containing compound of $R_f$—X—A—H, a compound of Z—A'—H may be used to convert the —NCO groups to —NHCOA'Z groups. For instance, with a view to further improving the durability by providing adequate bonding to the surface of the synthetic fibers, it is possible to obtain a final compound having at least one —NHCOA'Z group. In such a case, it is particularly preferred that Z—A'—H is an alcohol wherein A' is —O— or an amine wherein A' is —N(Z')—. With a view to imparting an affinity with the synthetic fiber surface, Z—A'—H may be a combination of an alkanol amine, a diamine or ammonia with a methylol-forming agent as well as an alcohol such as

Further, it is also possible to obtain a stainproofing agent having especially superior water repellency by using a straight chain stearyl group-containing compound such as n—$C_{18}H_{37}OH$, n—$C_{18}H_{37}NH_2$ or n—$C_{18}H_{37}SH$, as Z—A'—H. In the process of the present invention, it is, of course, possible to use as Z—A'—H a plurality of compounds wherein Z and A' are different.

By the above-mentioned reaction, it is possible to obtain a mixture of PFA group-containing compounds having at least one —NHCOAX$R_f$ group, a molecular weight of at most 8000 and, if required, a —NHCOA'Z group, provided that the total of the —NHCOAX$R_f$ groups and the —NHCOA'Z groups is at least three. Such PFA group-containing compounds should preferably have a molecular weight of from 1500 to 5000, more preferably from 2000 to 4000. If the molecular weight is too great, the durability of the stainproofing effect tends to be poor, and there will be difficulties in the application for use prior to the dyeing step or during the spinning of the base yarns. The derivatives of the present invention obtained from the mixture of polyfunctional isocyanate compounds are superior in the above-mentioned durability to derivatives obtained from difunctional isocyanate compounds such as the fluorine-containing urethane compounds having a relatively low molecular weight.

In the present invention, the mixture of PFA group-containing compounds (hereinafter referred to simply as a "PFA mixture") comprises compounds containing at least one PFA group in the form of a —NHCOAX$R_f$ group. The respective PFA group-containing compounds constituting the PFA mixture, may be those wherein all of the —NCO groups in the polyfunctional isocyanate compounds in the isocyanate mixture as the starting material are converted to —NHCOAX$R_f$ groups. Usually, however, the compounds may be those wherein at least one of the at least three —NCO groups is converted to a —NHCOAX$R_f$ group. In the latter case, the rest of the —NCO groups are converted to 'NHCOA'Z groups. It is usually preferred that the PFA group-containing compounds contain at least one —NHCOAXR$_f$ group and at least one —NHCOA'Z group. In a preferred embodiment, the polyfunctional isocyanate compounds in the isocyanate mixture as the starting material contain from 3 to 15, preferably from 3 to 8, —NCO groups, and accordingly the respective PFA group-containing compounds in the PFA mixture contain from 1 to 14, preferably from 1 to 10, —NHCOAXR$_f$ groups and from 1 to 14, preferably from 1 to 10, —NHCOA'Z groups. The PFA group-containing compounds in the PFA mixture may, of course, be different from one another in the number and type of the —NHCOAXR$_f$ groups or the number and the type of the —NHCOA'Z groups.

The process of the present invention is conducted by reacting R$_f$—X—A—H and Z—A'—H to the isocyanate mixture in the respective molar amounts corresponding to the molar amount of —NCO groups. From the viewpoints of the yield of the desired product and the reaction rate, it is preferred to employ a method wherein firstly a predetermined amount of R$_f$—X—A—H is reacted to the isocyanate mixture and then an excess amount of Z—A'—H is reacted thereto. However, it is, of course, possible to reverse the order of the reactions or to react them simultaneously.

The reaction of the isocyanate mixture with R$_f$—X—A—H may be conducted under various reaction conditions in various manners with use of various reaction apparatus. For instance, in a case where R$_f$—X—A—H is a fluorine-containing alcohol, the reaction is usually conducted at a temperature of from 0° to 200° C., preferably from 40° to 100° C. The reaction is preferably conducted in an inert organic solvent. However, in certain cases, the reaction can be conducted without using an inert organic solvent. As the inert organic solvent suitable for use in the reaction, a solvent capable of dissolving the isocyanate mixture is preferred, and as such a solvent, there may be mentioned a halogenated hydrocarbon such as 1,1,1-trichloroethane, trichloroethylene, trichloromethane or trichlorofluoroethane; a hydrocarbon such as benzene, toluene or hexane; an ether such as dioxane, tetrahydrofuran, diethyl ether, dimethoxy ethane or diethylene glycol dimethyl ether; a ketone such as acetone, methylethyl ketone or methyl isobutylketone; an ester such as ethylacetate or butylacetate; dimethylformamide; dimethylsulfoxide; or acetonitrile. By using such an inert organic solvent, a uniform reaction can efficiently and advantageously be carried out. The inert organic solvent is usually used in an amount of from 1 to 50 moles, preferably from 5 to 20 moles, per mole of the isocyanate mixture. In this reaction, the molar ratio of the fluorine-containing alcohol to the isocyanate mixture is properly selected depending upon the desired number of —NHCOAXR$_f$ groups in the intended PFA group-containing compounds. For instance, if it is intended to obtain the final compounds containing one —NHCOAXR$_f$ group, the fluorine-containing alcohol is used in an amount of about 1 mole per mole of the isocyanate mixture, and usually in an amount of from 0.5 to 2 moles, preferably from 0.8 to 1.3 moles.

Likewise, for the reaction with Z—A'—H, various reaction conditions, reaction operation and reaction apparatus may be employed. From the viewpoint of the operation, however, it is preferred to employ a method wherein an excess amount of Z—A'—H is added relative to the remaining —NCO groups in the reaction mixture of the above-mentioned reaction, and the reaction is continuously carried out in the same condition as above. It is, of course, desirable to select the optimum condition depending upon e.g. the type of the starting materials, for instance, by changing the reaction temperature.

The above-mentioned reactions for conversion to —NHCOAXR$_f$ groups and —NHCOA'Z groups are preferably conducted under substantially anhydrous condition to effectively prevent the side reaction. Namely, the presence of water is disadvantageous to the —NCO group. For instance, adequate control of water should be conducted with respect to the starting materials and the reaction apparatus, and the reaction is preferably conducted in an inert gas stream such as dried nitrogen. Further, such a reaction can be efficiently and advantageously conducted in the presence of a salt of an alkyl tin such as dibutyl tin dilaurate or in the presence of a catalyst composed of a compound having a pKa of at least 5.0, preferably from 7 to 10. As such as catalyst, there may be used various kinds of catalysts. For instance, there may suitably be used tertiary amines such as trimethylamine, triethylamine, tripropylamine, tributylamine, triallylamine, N-methylpiperidine, N-methylpyrrolidine, N-methylmorpholine, N-ethylmorpholine, N,N-dimethylbenzylamine, pyridine, 4-methylpyridine, dimethyl laurylamine, dimethylmyristylamine, dimethylstearylamine, tricaprylamine, methyldistearylamine, methyldilaurylamine, dimethylcaprylamine, dimethylpalmitylamine, tetramethylpropylenediamine and pentamethyldiethylenetriamine. In addition to these tertiary amines, there may be used as the catalyst, an alkali-metal alcoholate and an inorganic alkali metal salt, an inorganic alkaline earth metal salt, an ammonium salt, an inorganic salt of metal such as tin, cobalt, iron, titanium, zinc, antimony or lead or an organic salt having a pKa of at least 0.5. The amount of the catalyst is usually selected within a range of from 0.001 to 10 parts by weight, preferably from 0.1 to 3 parts by weight, per 100 parts by weight of the isocyanate mixture as the starting material.

In the present invention, the PFA group-containing compounds or the mixture of the PFA group-containing compounds may be used in the form of an organic solution or an organic dispersion. However, for the application to the dyeing step, they are preferably used in the form of an aqueous dispersion. In this case, as the dispersing agent, various surfactants such as nonionic, anionic, cationic or amphoteric surfactants may be used. These surfactants may be used in a proper combination. To facilitate the dispersion of the PFA group-containing compounds, an organic solvent may be incorporated. Further, when a PFA group-containing compounds or a mixture of PFA group-containing compounds is to be dispersed in a medium mainly composed of water, it may be dispersed in the presence of a fluorine-type surfactant such as a hydrophilic group-containing urethane compound represented by the general formula of R$_f$—X—A—CONH—Y—NHCO—T where R$_f$, X and A are as defined above, Y is a divalent organic group and T is a hydrophilic group. As T, there may be used various groups, for instance, a nonionic group represented by the formula of —(CH$_2$CH$_2$O)$_l$—R$^3$ where l is an integer of 1 to 50, and R$^3$ is a hydrogen atom or a lower alkyl group having from 1 to 4 carbon atoms; an anionic group such as —(CH$_2$CH$_2$O)$_l$—SO$_3$M where M is a hydrogen atom, an alkali metal or an ammonium group, —(CH$_2$CH$_2$O)$_l$—PO$_3$M, —CH₂CH₂SO₃M or —CH₂CH₂COOM; or a cationic group such as —CH₂CH₂N⊕R⁴R⁵R⁶X⊖ where each of R⁴, R⁵ and R⁶ is an alkyl group or an aryl group. X is chlorine, bromine, iodine or OCOCH₃. From the viewpoint of usefulness in combination with other treating agents, however, the nonionic group such as —(CH₂CH₂O)₂₂—CH₃ is preferably used. When such a hydrophilic group-containing urethane compound is incorporated, the weight ratio of the PFA group-containing compound/the hydrophilic group-containing urethane compound is selected within a range of from 99/1 to 25/75, preferably from 95/5 to 50/50.

As the organic solvent to be incorporated at the time of dispersing the PFA group-containing compound or the PFA mixture into water, there may be mentioned a water-soluble ether such as dioxane, tetrahydrofuran or ethylpropylether; a water-soluble glycol ether such as diethylene glycol dimethylether, diethylene glycol diethylether, ethylene glycol monomethylether, ethylene glycol monoethylether, ethylene glycol monopropylether, ethylene glycol monobutylether, ethylene glycol monophenylether, diethylene glycol monomethylether, diethylene glycol monoethylether, diethylene glycol monopropylether, diethylene glycol monobutylether, triethylene glycol monomethylether, triethylene glycol monoethylether, triethylene glycol monopropylether or triethylene glycol monobutylether; an amide such as formamide, dimethyl formamide or acetoamide; a ketone such as acetone, methylethyl ketone, methylisopropyl ketone, methylisobutyl ketone or diacetone alcohol; an alcohol such as methanol, ethanol, propanol or butanol; and an ester such as methylacetate, ethylacetate, propylacetate or butylacetate. The amount of such an organic solvent is usually selected within a range of from 10 to 300 parts by weight, preferably from 20 to 150 parts by weight, per 100 parts by weight of the PFA group-containing compound or the PFA mixture.

As is apparent from the afore-mentioned specific examples, there is no particular restriction to W so long as it is a trivalent organic group. Namely, for example, W may be illustrated by the following trifunctional isocyanate compounds of W(NCO)₃:

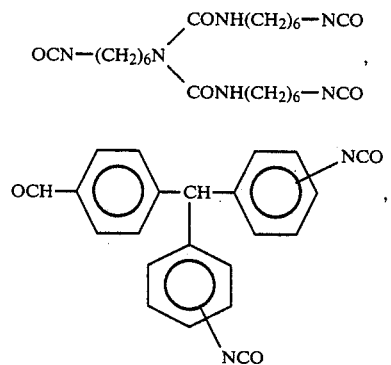

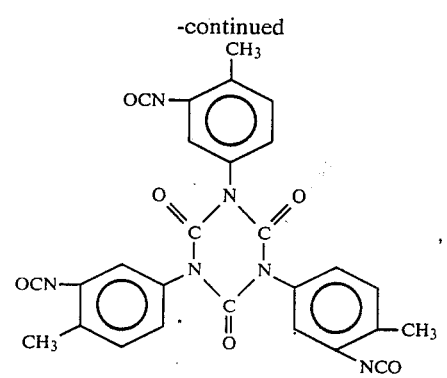

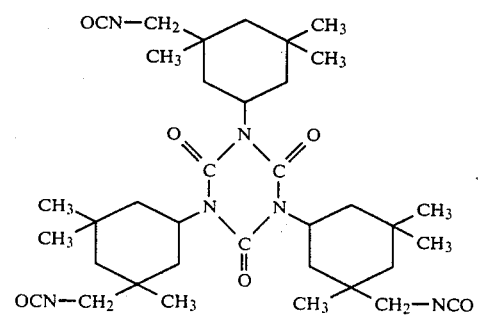

Thus, W may be selected from a wide range. The selection of the trifunctional isocyanate compound of the formula W(NCO)₃ is usually made in consideration of the availability or the molecular weight of the desired PFA group-containing compound.

Further, as the above-mentioned $R_f$—X—A—H, a $R_f$—R—OH type fluorine-containing alcohol is usually preferably employed. By using as the starting material a mixture of a plurality of fluorine-containing alcohols wherein the carbon number in $R_f$ or R is different from one another, it is also possible to obtain the PFA group-containing compounds in the form of a mixture.

In the present invention, when the PFA group-containing compound or the PFA mixture is to be dispersed in a medium composed mainly of water to obtain an aqueous dispersion, various methods may be employed for the preparation of the dispersion. For instance, there may be mentioned a method in which a mixture of the PFA group-containing compound or the PFA mixture, an emulsifier (i.e. a surfactant) and an aqueous medium, is stirred at a high speed under heating, and then cooled to room temperature, a method wherein an organic solvent solution of the PFA group-containing compound or the PFA mixture (in some cases, an emulsifier is added) is dropwise added into an aqueous solution of an emulsifier under stirring, a method wherein an aqueous solution of an emulsifier is dropwise added to an organic solvent solution of the PFA group-containing compound or the PFA mixture under stirring, a method wherein an organic solvent solution of the PFA group-containing compound or the PFA mixture and an emulsifier is dropwise added into water under stirring, or a method wherein water is dropwise added to such an organic solvent solution under stirring.

When the stainproofing agent of the present invention is prepared in the form of an aqueous dispersion, the solid concentration is not so critical, but is usually adjusted to be from 5 to 60% by weight, preferably from 15 to 50% by weight. In the actual processing, this dispersion is further diluted with water to have a solid concentration of from 0.1 to 4% by weight. Such an aqueous dispersion type stainproofing agent is advantageous over the organic solvent type in that it has a higher ignition point and it is possible to increase the solid concentration and further in that the environmental pollution for the processing operation can thereby be minimized.

The stainproofing agent of the present invention can be advantageously applied to various articles made of polyamide, polyester, leather or wood, for instance, not only to interior products such as carpets, living room sets, curtains, wall papers or interior articles of vehicles, but also to exterior products such as outdoor tents. It is particularly useful as a stainproofing agent for synthetic fibers, and has a feature that it is applicable prior to the dyeing step or during the spinning of the base yarns.

As the method for the application of the stainproofing agent of the present invention, there is no particular restriction, and various conventional or well known methods may be employed. For instance, it may be applied in such a manner that it is deposited or impregnated on the surface of the article to be treated by means of a conventional application method such as immersion, spraying or coating and then dried. Further, in the application, various other treating agents or additives such as an antistatic agent, a moth-proofing agent, a flame retardant, a dyestuff stabilizer or a wrinkle-preventive agent, may be used in combination.

The stainproofing agent of the present invention has the following advantages. Namely, it has superior water repellency, and when used as a treating agent for spinning, it is capable of imparting an excellent property to the fibers, whereby it has a good stainproofing property and high abrasion durability. Further, it has good compatibility with a spinning solution. Especially when it is prepared in the form of an aqueous dispersion, it has high stability, whereby the treating agent does not fall off during the dyeing operation, thus providing satisfactory dyeing.

Now, the present invention will be described in further detail with reference to Examples.

However, it should be understood that the present invention is by no means restricted by these specific examples. Unless otherwise specified, "%" or "parts" mean "% by weight" and "parts by weight".

In the following Examples and Comparative Examples, the water repellency and the oil repellency were measured in the following manners. Namely, in Examples 1 to 9 and 17 to 20 and Comparative Examples 1 and 2. The water repellency was evaluated by placing a few drops of a mixed solution comprising 20 parts by volume of isopropanol and 80 parts by volume of water on a sample cloth at two locations, and the water repellency was represented by the time required for the solution to soak into the cloth. In the rest of the Examples and Comparative Examples, water repellency was evaluated by placing a few drops of the aqueous isopropanol solution having a composition as shown in the following Table 1, on a test cloth, and the water repellency was represented by the point representing the maximum concentration at which the aqueous solution was maintained without soaking into the cloth. The oil repellency was determined by placing a few drops (a diameter of about 4 mm) of the test solution as shown in the following Table 2, on a sample cloth at two locations, and evaluating the infiltration condition upon expiration of 30 seconds (AATCC-TM 118-1966).

TABLE 1

| Water repellency | Isopropanol concentration (% by volume) in an aqueous isopropanol solution |
|---|---|
| 5 | 40 |
| 4 | 30 |
| 3 | 20 |
| 2 | 10 |
| 1 | 0 |
| 0 | Incapable of maintaning water drops |

TABLE 2
(AATCC-TM 118-1966)

| Oil repellency | Test solution | Surface tension dyne/cm 25° C. |
|---|---|---|
| 8 | n-Heptane | 20.0 |
| 7 | n-Octane | 21.8 |
| 6 | n-Decane | 23.5 |
| 5 | n-Dodecane | 25.0 |
| 4 | n-Tetradecane | 26.7 |
| 3 | n-Hexadecane | 27.3 |
| 2 | Hexadecane 35/Nujol 65 mixed solution | 29.6 |
| 1 | Nujol | 31.2 |
| 0 | Poorer than 1 | |

For the determination of the stainproofing property, a sample cloth was cut into a sample of 5×7 cm, and the sample and a dry dust as shown in the following Table 3 (in an amount twice the weight of the sample) were put in a container and vigorously mixed for 3 minutes for staining. After the staining operation, an excess dust was removed by an electric cleaner, and the reflectance was measured to evaluate the staining rate. The staining rate was calculated in accordance with the following equation.

Staining rate (%) = $(R_o - R)/R_o \times 100$ $R_o$: Reflectance of non-stained cloth
Reflectance of stained cloth

TABLE 3

| Dust | % by Weight |
|---|---|
| Peat moss | 38 |
| Cement | 17 |
| Kaolin clay | 17 |
| Silica | 17 |
| Carbon black | 1.75 |
| Ferric oxide | 0.50 |
| Mineral oil | 8.75 |

Synthesis 1

Into a four necked flask having an internal capacity of 500 ml and equipped with a stirrer, a dropping funnel, a thermometer and a condenser, 95.6 g (0.2 mole) of

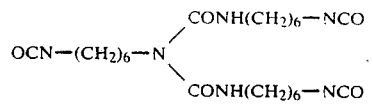

0.3 g of $(C_4H_{10})_2Sn(OCOC_{11}H_{23})_2$ and 100 g of dioxane were fed. While maintaining the temperature at 80° C., 205.6 g (0.4 mole) of $C_nF_{2n+1}CH_2CH_2OH$ (where n is a mixture of 6, 8, 10 and 12, and has a average value of 9.0) was dropwise added in 2 hours by means of the dropping funnel. Then, the reaction temperature was lowered to 60° C., and 14.8 g (0.2 mole) of

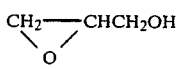

was added. The reaction was conducted for 1 hour. The reaction rate was 100%.

Synthesis 2

| | |
|---|---|
| $R_f$ compound of Synthesis 1 | 10 parts |
| Butyl acetate | 15 parts |
| PBC-44 (Nonionic emulsifier manufactured by Nikko Chemical Co.) | 2 parts |
| Tween 80 Nonionic emulsifier manufactured by Kao Atlas Co.) | 2 parts |
| Famin DMC (Cationic emulsifier manufactured by Kao Soap Co., Ltd.) | 1 part |
| Water (Deionized water) | 70 parts |

The above mixture was stirred at 80° C. for 30 minutes at 1000 rpm and pre-emulsified, and then emulsified at 60° C. for 30 minutes by means of a homogenizer, whereupon a treating agent composed of an aqueous latex was obtained.

EXAMPLE 1

The aqueous latex of Synthesis 2 was diluted with deionized water to bring the solid content to 0.5% by weight. A nylon knitted cloth was immersed in the emulsion for 2 seconds, and then the cloth was squeezed between two rubber rollers to bring the wet pick-up to 90%. Then, the cloth was dried at 100° C. for 3 minutes. With respect to the treated cloth thus obtained, the initial water repellency and oil repellency and the stainproofing property were measured. The results are shown in Table 4.

Then, the following dyeing solution was fed in a pot of a Color Pet (manufactured by Nippon Senshoku Kikai K.K.), and the above treated cloth was put in a holder. After raising the temperature to 100° C., it was dyed for 60 minutes.

| | |
|---|---|
| Dyestuff (Suminol Leveling Sky Blue R: acid dye manufactured by Sumitomo Chemical Co., Ltd.) | 1% owf |
| $(NH_4)_2SO_4$ | 3% owf |
| Dyeing assistant (Disper SV: anionic dispersing agent manufactured by Meisei Chemical Industry Co.) | 1% owf |
| Bath ratio (1:20) | |

The dyed cloth was washed with water for 10 minutes, and then dried at 85° C. for 10 minutes. The water repellency and oil repellancy and the stainproofing property of the dyed cloth thereby obtained were measured. The results are shown in Table 4.

EXAMPLE 2 TO 9

Each of the $R_f$ compounds shown in Table 4 prepared in the same manner as in Synthesis 1 was made into an aqueous dispersion in the same manner as in Synthesis 2. A nylon knit cloth was treated in the same manner as in Example 1, whereupon the water repellency and the stainproofing property of the treated cloth were measured. The results are shown in Table 4.

COMPARATIVE EXAMPLES 1 AND 2

With respect to the $R_f$ compounds derived from difunctional isocyanate compounds as shown in Table 4, the properties were measured in the same manner as in Examples 1 to 9. The results are shown in Table 4.

TABLE 4

| | | Initial | | | After dyeing | | |
|---|---|---|---|---|---|---|---|
| $R_f$ Compounds | | Water repellency | Oil repellency | Stainproofing property | Water repellency | Oil repellency | Stainproofing property |
| Example 1 | $R_fCH_2CH_2OCONH(CH_2)_6N\begin{cases}CONH(CH_2)_6NHCOOCH_2CH_2R_f\\CONH(CH_2)_6NHCOOCH_2CH_2CH\text{---}CH_2\diagdown O\diagup\end{cases}$ | More than 3 min. | 6 | 8 | More than 3 min. | 6 | 8 |
| Example 2 | $R_fCH_2CH_2OCONH(CH_2)_6N\begin{cases}CONH(CH_2)_6NHCOOCH_2CH_2R_f\\CONH(CH_2)_6NHCONHCH_2CH_2OH\end{cases}$ | More than 3 min. | 6 | 8 | More than 3 min. | 6 | 8 |
| Example 3 | $R_fCH_2CH_2OCONH(CH_2)_6N\begin{cases}CONH(CH_2)_6NHCOOCH_2CH\text{---}CH_2\diagdown O\diagup\\CONH(CH_2)_6NHCOOCH_2CH\text{---}CH_2\diagdown O\diagup\end{cases}$ | More than 3 min. | 6 | 7 | More than 3 min. | 6 | 7 |
| Example 4 | $R_fCH_2CH_2OCONH(CH_2)_6N\begin{cases}CONH(CH_2)_6NHCOOCH_2CH_2R_f\\CONH(CH_2)_6NHCOOCH_3\end{cases}$ | More than 3 min. | 6 | 7 | More than 3 min. | 6 | 7 |

TABLE 4-continued

| $R_f$ Compounds | | Initial Water repellency | Initial Oil repellency | Initial Stainproofing property | After dyeing Water repellency | After dyeing Oil repellency | After dyeing Stainproofing property |
|---|---|---|---|---|---|---|---|
| Example 5 | 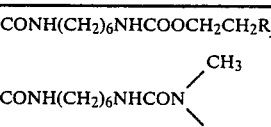 | More than 3 min. | 6 | 6 | More than 3 min. | 5 | 5 |
| Example 6 | 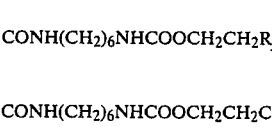 | More than 3 min. | 6 | 5 | More than 3 min. | 6 | 5 |
| Example 7 | 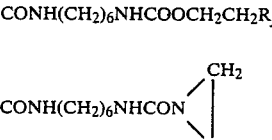 | More than 3 min. | 6 | 5 | More than 3 min. | 6 | 5 |
| Example 8 | 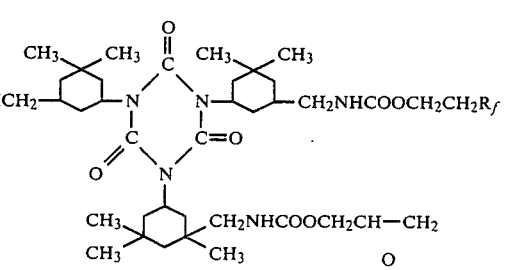 | More than 3 min. | 6 | 5 | More than 3 min. | 6 | 5 |
| Example 9 | 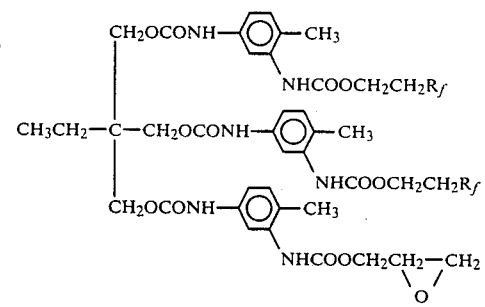 | More than 3 min. | 6 | — | More than 3 min. | 5 | — |
| Comparative Example 1 | 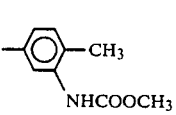 | More than 3 min. | 6 | 5 | 2 min. | 2 | 5 |
| Comparative Example 2 | 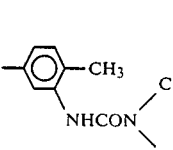 | More than 3 min. | 6 | 5 | 2 min. | 2 | 4 |

In the above Table 4, $R_f$ is $C_nF_{2n+1}$ (where n is a mixture of 6, 8, 10 and 12, and has an average value of 9.0).

Synthesis 3

Into a four necked flask having an internal capacity of 500 ml and equipped with a stirrer, a dropping funnel, a thermometer and a condenser, 95.6 g (0.2 mole) of

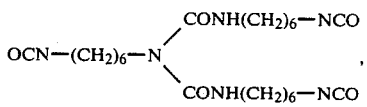

0.3 g of $(C_4H_{10})_2Sn(OCOC_{11}H_{23})_2$ and 100 g of dioxane were fed. While maintaining the temperature at 80° C., 205.6 g (0.4 mole) of $C_nF_{2n+1}CH_2CH_2OH$ (where n is a mixture of 6, 8, 10 and 12, and has an average value of 9.0) was dropwise added in 2 hours by means of the dropping funnel. Then, the reaction temperature was lowered to 60° C., and 54.0 g (0.2 mole) of n—$C_{18}H_{37}OH$ was added. The reaction was conducted for 1 hour. The reaction rate was 100%. The analysis of the product was conducted by gel permeation chromatography and nuclear magnetic resonance spectrum.

| Synthesis 4 | |
|---|---|
| $R_f$ compound of Synthesis 3 | 10 parts |
| Butyl acetate | 15 parts |
| PBC-44 (Nonionic emusifier manufactured by Nikko Chemical Co.) | 2 parts |
| Tween 80 (Nonionic emulsifier manufactured by Kao Atlas Co.) | 2 parts |
| Famin DMC (Cationic emulsifier manufactured by Kao Soap Co., Ltd.) | 1 part |
| Water (Deionized water) | 70 parts |

The above mixture was stirred at 80° C. for 30 minutes at 1000 rpm and pre-emulsified, and then emulsified at 60° C. for 30 minutes by means of a homogenizer, whereby a treating agent composed of an aqueous latex was obtained.

EXAMPLE 10

The aqueous latex of Synthesis 4 was diluted with deionized water to bring the solid content to 0.5% by weight. A nylon knitted cloth was immersed in the emulsion for 2 seconds, and the cloth was squeezed between two rubber rollers to bring the wet pick-up to 90%. Then, the cloth was dried at 100° C. for 3 minutes.

With respect to the treated cloth thus obtained, the initial water repellency and oil repellency and the stainproofing property were measured. The results are shown in Table 5.

Then, the following dyeing solution was fed in a pot of Color Pet (manufactured by Nippon Senshoku Kikai K.K.), and the above treated cloth was put in a holder. After raising the temperature to 100° C., the cloth was dyed for 60 minutes.

| | |
|---|---|
| Dyestuff (Suminol Leveling Sky Blue R: acid dye manufactured by Sumitomo Chemical Co., Ltd.) | 1% owf |
| $(NH_4)_2SO_4$ | 3% owf |
| Dyeing assistant (Disper SV: anionic dispersing agent manufactured by Meisei Chemical Co.) | 1% owf |
| Bath ratio (1:20) | |

The dyed cloth was washed with water for 10 minutes, and then dried at 85° C. for 10 minutes. The water repellency and oil repellency and the spainproofing property of the dyed cloth thus obtained were measured. The results are shown in Table 5.

EXAMPLES 11 TO 16

Each of the $R_f$ compounds as shown in Table 5 prepared in the same manner as in Synthesis 3, was made into an aqueous dispersion in the same manner as in Synthesis 4. A nylon knitted cloth was treated in the same manner as in Example 10, whereupon the water repellency and oil repellency and the stainproofing property of the cloth were measured. The results are shown in Table 5.

COMPARATIVE EXAMPLES 3 AND 4

With respect to the $R_f$ compounds derived from the difunctional isocyanate compounds as shown in Table 5, the properties were measured in the same manner as in Examples 10 to 16. The results are shown in Table 5.

TABLE 5

| | $R_f$ Compound | Initial | | | After dyeing | | |
|---|---|---|---|---|---|---|---|
| | | Water repellency | Oil repellency | Stainproofing property | Water repellency | Oil repellency | Stainproofing property |
| Example 10 | $R_fCH_2CH_2OCONH(CH_2)_6N\begin{array}{c}CONH(CH_2)_6NHCOOCH_2CH_2R_f\\ CONH(CH_2)_6NHCOOC_{18}H_{37}\end{array}$ | 5 | 6 | 8 | 5 | 6 | 8 |
| Example 11 | $R_fCH_2CH_2OCONH(CH_2)_6N\begin{array}{c}CONH(CH_2)_6NHCOOC_{18}H_{37}\\ CONH(CH_2)_6NHCOOC_{18}H_{37}\end{array}$ | 5 | 5 | 9 | 5 | 5 | 9 |

TABLE 5-continued

| $R_f$ Compound | Initial | | | After dyeing | | |
|---|---|---|---|---|---|---|
| | Water repellency | Oil repellency | Stainproofing property | Water repellency | Oil repellency | Stainproofing property |
| Example 12:<br>$R_fCH_2CH_2OCONHCH_2$—[cyclohexyl(CH_3)_4]—N in triazine ring (C=O)_3 with two other substituted cyclohexyl-CH_2NHCOOC_{18}H_{37} groups | 5 | 5 | 9 | 5 | 5 | 0 |
| Example 13:<br>$CH_3CH_2$—C(—CH_2OCONH—C_6H_3(CH_3)(NHCOOCH_2CH_2R_f))(—CH_2OCONH—C_6H_3(CH_3)(NHCOOC_{18}H_{37}))(—CH_2OCONH—C_6H_3(CH_3)(NHCOOC_{18}H_{37})) | 4 | 5 | 9 | 5 | 5 | 0 |
| Example 14:<br>$R_fCH_2CH_2OCONH(CH_2)_6N$(CONH(CH_2)_6NHCOOC_{18}H_{37})(CONH(CH_2)_6NHCOOCH_2CH—CH_2 with epoxide O) | 5 | 6 | — | 5 | 6 | 7 |
| Example 15:<br>$R_fCH_2CH_2OCONH(CH_2)_6N$(CONH(CH_2)_6NHCOOCH_2CH_2R_f)(CONH(CH_2)_6NHCONHC_{18}H_{37}) | 5 | 6 | 8 | 5 | 6 | 8 |
| Example 16:<br>$R_fCH_2CH_2OCONH(CH_2)_6N$(CONH(CH_2)_6NHCOOCH_2CH_2R_f)(CONH(CH_2)_6NHCOSC_{18}H_{37}) | 5 | 6 | 8 | 5 | 6 | 8 |
| Comparative Example 3:<br>$R_fCH_2CH_2OCONH$—C_6H_3(CH_3)(NHCOOCH_3) | 3 | 5 | 8 | 3 | 2 | 5 |
| Comparative Example 4:<br>$R_fCH_2CH_2OCONH$—C_6H_3(CH_3)(NHCON(CH_3)_2) | 3 | 6 | 8 | 3 | 2 | 4 |

In the above Table 5, $R_f$ is $C_nF_{2n+1}$ (where n is a mixture of 6, 8, 10 and 12, and has an average value of 9.0).

Synthesis 5

Into a four necked flask having an internal capacity of 500 ml and equipped with a stirrer, a dropping funnel, a thermometer and a condenser, 100 g of Desmodur-TPKL (hexamethylenediisocyanate polymer which contains 40% of a trimer and 22.6% of isocyanate, manufactured by Sumitomo-Bayer Co.), 0.3 g of Bu$_2$Sn(OCOC$_{11}$H$_{23}$)$_2$ and 100 g of dioxane were fed. While maintaining the temperature at 70° C., 224 g of $C_nF_{2n+1}CH_2CH_2OH$ (where n is a mixture of 6, 8, 10 and 12, and has an average value of 9.0) was dropwise added in 2 hours by means of the dropping funnel. Then, the reaction temperature was lowered to 60° C., and 9.3 g of

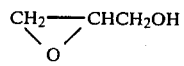

was added. The reaction was conducted for 1 hour. The reaction rate was 100%. The reaction rate was confirmed by gas chromatography and infrared spectrophotometry. The product was analyzed by GPC.

Syntheses 6 and 7

The Synthesis were conducted in the same manner as in Synthesis 5. The results are shown in Table 6.

TABLE 6

| Syntheses | Isocyanate polymers | $R_f$—X—A—H | Z—A'—H | Reaction rate |
|---|---|---|---|---|
| 6 | Desmodur-TPKL 100 g | $C_nF_{2n+1}C_2H_4OH$ 224 g | $C_{18}H_{37}OH$ 41.2 g | 100% |
| 7 | Desmodur-TPKL 100 g | $C_8F_{17}SO_2\underset{\underset{CH_3}{\mid}}{N}C_2H_4OH$ 235.8 g | CH$_2$—CHCH$_2$OH (epoxide) 41.2 g | 100% |

Synthesis 8

Into a four necked flask having an internal capacity of 2 l and equipped with a stirrer, a dropping funnel, a thermometer and a condenser, 348 g of toluene, 2,4-diisocyanate was fed. While maintaining the temperature at 90° C., 10.8 g of distilled water was dropwise added in 5 hours. The temperature was raised to 140° C. and the reaction was conducted for 3 hours. The reaction product contained 26.0% of isocyanate.

The temperature was brought to 70° C., and 350 g of dioxane was added. Then, 900 g of $C_nF_{2n+1}C_2H_4OH$ (where n is a mixture of 6, 8, 10 and 12, and has an average value of 9.0) was dropwise added in 2 hours by means of the dropping funnel. Then, the reaction temperature was lowered to 60° C., 37.2 g of

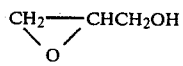

was added. The reaction was conducted for 1 hour. The reaction rate was 100%. The reaction rate was confirmed by gas chromatography and infrared spectrophotometry. The product was analyzed by GPC.

| EXAMPLES 17 to 20: | |
|---|---|
| Compound of each of Syntheses 5 to 8 | 10 parts |
| Butyl acetate | 15 parts |
| PBC-44 (Nonionic emulsifier manufactured by Nikko Chemical Co.) | 2 parts |
| Tween 80 (Nonionic emulsifier manufactured by Kao Atlas Co.) | 2 parts |
| Famin DMS (Cationic emulsifer manufactured by Kao Soap Co., Ltd.) | 1 part |
| Water (Deionized water) | 70 parts |

The above mixture was stirred at 80° C. for 30 minutes at 1000 rpm and pre-emulsified, and then emulsified at 60° C. for 30 minutes by means of a homogenizer, whereby a treating agent composed of an aqueous latex was obtained. This dispersion was diluted with deionized water to bring the solid content to 0.5% by weight. A nylon knitted cloth was immersed in the emulsion for 2 seconds, and the cloth was squeezed through two rubber rollers to bring the wet pick-up to 90%. Then, the cloth was dried at 100° C. for 3 minutes. With respect to the treated cloth thus obtained, the initial water repellency and oil repellency and the stainproofing property was measured. The results are shown in Table 7.

| | |
|---|---|
| Dyestuff (Suminol Leveling Sky Blue R: acid dye manufactured by Sumitomo Chemical Co., Ltd.) | 1% owf |
| (NH$_4$)$_2$SO$_4$ | 3% owf |
| Dyeing assistant (Disper SV: anionic dispersing agent manufactured by Meisei Chemical Co.) | 1% owf |
| Bath ratio (1:20) | |

The above dyeing solution was fed in a pot of Color Pet (manufactured by Nippon Senshoku Kikai K.K.), and the above nylon knitted cloth was put in a holder. After raising the temperature to 100° C., the cloth was dyed for 60 minutes. The dyed cloth was washed with water for 10 minutes, and then dried at 85° C. for 10 minutes. The water repellency and oil repellency and the anti-dry soil property of the nylon cloth thus obtained, were measured. The results are shown in Table 7.

TABLE 7

| | Initial | | | After dyeing | | |
|---|---|---|---|---|---|---|
| Examples | Water repellency | Oil repellency | Stainproofing property | Water repellency | Oil repellency | Stainproofing property |
| 17 | More than 3 minutes | 6 | 7 | More than 3 minutes | 6 | 8 |
| 18 | More than 3 minutes | 6 | 8 | More than 3 minutes | 6 | 9 |
| 19 | More than 3 minutes | 5 | 9 | More than 3 minutes | 5 | 10 |
| 20 | More than 3 minutes | 5 | 9 | More than 3 minutes | 5 | 10 |

We claim:
1. A stainproofing agent containing as an active ingredient a polyfluoroalkyl-containing compound of the following formula and having a molecular weight of from 800 to 3000:

wherein
$R_f$ is a polyfluoroalkyl group having from 1 to 20 carbon atoms,
X is —R—, —CON(R$^1$)—Q— or —SO$_2$N(R$^1$)—Q—, wherein R is alkylene, R$^1$ is a hydrogen atom or a lower alkyl group and Q is alkylene,
—A′—Z is selected from the group consisting of

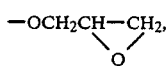

—OR′, —OCH$_2$CH$_2$CN, —OCH$_2$CH$_2$NO$_2$, —OCH$_2$C-H$_2$OH, —NHCH$_2$OH, —NHCH$_2$CH$_2$OH,

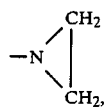

—NHR′, —NR′R′, —N(CH$_2$CH$_2$OH)$_2$ and

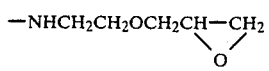

wherein R′ is an alkyl group,
A is —O—, —S— or —N(Z′)— wherein Z′ is H or lower alkyl,
W is selected from the group consisting of

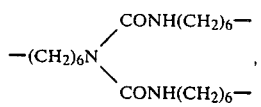

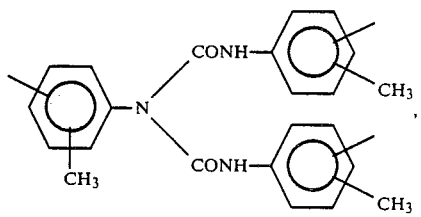

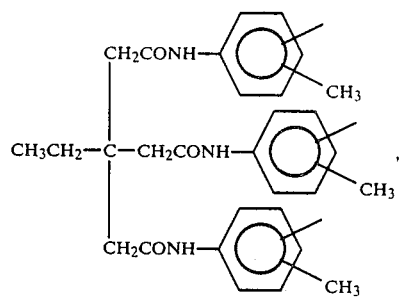

-continued

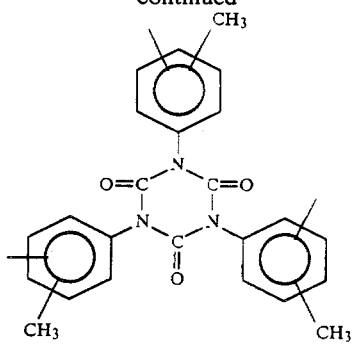

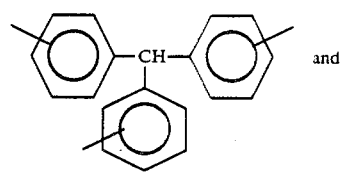

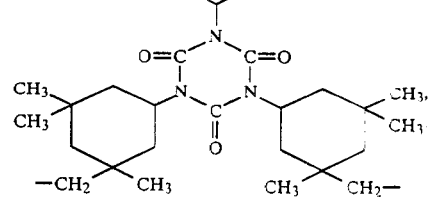

and a is an integer of 1, 2 or 3.
2. The stainproofing agent according to claim 1, wherein
$R_f$ is a perfluoroalkyl group of the formula $C_nF_{2n+1}$ wherein n is 4 to 16,
X is an alkylene of the formula $C_mH_{2m}$ wherein m is 1 to 10,
A is —O—, and
a is 1 or 2.
3. The stainproofing agent according to claim 1, wherein the polyfluoroalkyl group-containing compound is represented by the formula:

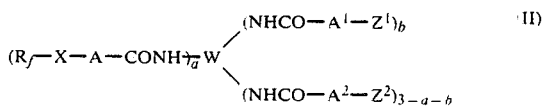

wherein
$R_f$, X, A and W are as defined in claim 1,
A$^1$ is —O—, —S— or —N(Z′)—,
wherein
Z′ is as defined in claim 1,
Z$^1$ is a straight chain stearyl group,
A$^2$-Z$^2$ is selected from the group consisting of

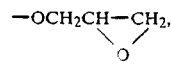

—OR′, —OCH$_2$CH$_2$CN, —OCH$_2$CH$_2$NO$_2$, —OCH$_2$C-H$_2$OH, —NHCH$_2$OH, —NHCH$_2$CH$_2$OH,

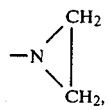

—NHR′, —NR′R′, —N(CH₂CH₂OH)₂ and

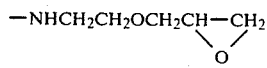

wherein R′ is an alkyl group, a is 1 or 2, and b is 1 or 2.

4. The stainproofing agent according to claim 3, wherein $R_f$ is a perfluoroalkyl group of the formula $C_nF_{2n+1}$ wherein n is 4 to 16, X is an alkylene of the formula $C_mH_{2m}$ wherein m is 1 to 10, A is —O—, and $A^1$ is —O—.

5. A process for preparing a stainproofing agent, which comprises reacting a mixture of polyfunctional isocyanate compounds having at least three —NCO groups and a —NHCON< bond derived from an addition reaction of a >H—N group-containing compound III with a —NCO group-containing compound IV, wherein the compound III is derived from OCH—Y—NCO, wherein Y is selected from the group consisting of —(CH₂)₆— and

and the compound IV is OCN—Y—NCO or derived from OCN—Y—NCO where Y is as defined above, with a compound of the formula $R_f$—X—A—H wherein $R_f$ is a polyfluoroalkyl group having from 1 to 20 carbon atoms, X is —R—, —CON(R¹)—Q— or —SO₂N(R¹)—Q—, wherein R is alkylene, $R^1$ is a hydrogen atom or a lower alkyl group and Q is a alkylene, and A is —O—, —S— or —N(Z′)— wherein Z′ is a hydrogen atom or a lower alkyl group, and, if required, further reacting the mixture with a compound of the formula Z—A′—H, wherein A′—Z is selected from the group consisting of

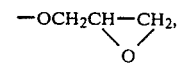

—OR′, —OCH₂CH₂CN, —OCH₂CH₂NO₂, —OCH₂CH₂OH, —NHCH₂OH, —NHCH₂CH₂OH,

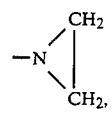

—NHR′, —NR′R′, —N(CH₂CH₂OH)₂ and

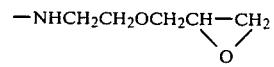

where R′ is an alkyl group, to form a mixture of polyfluoroalkyl containing compounds having at least one —NHCO—A—X—$R_f$ group wherein A, X and $R_f$ are as defined above, having a molecular weight of at most 8000 and, if required, at least one —NHCO—A′—Z group wherein A′—Z is as defined above, provided that the total of the —NHCO—A—X—$R_f$ groups and the number of —NHCO—A—Z groups is at least three.

6. The process of claim 7, wherein the mixture of polyfunctional isocyanate compounds is a mixture of polymers obtained by reacting diisocyanate compounds represented by the formula OCN—Y—NCO where Y is as defined in claim 5 with an active hydrogen-containing compound.

7. The process according to claim 5, wherein the mixture of polyfunctional isocyanates comprises from 10 to 90% by weight of a trifunctional isocyanate compound having three —NCO groups and from 10 to 90% by weight of polyfunctional isocyanate compounds having at least four —NCO groups.

* * * * *